United States Patent [19]
Davis et al.

[11] Patent Number: 6,071,434
[45] Date of Patent: Jun. 6, 2000

[54] PHOSPHINO DERIVATIVES

[75] Inventors: Keith Philip Davis, Kinver; Alan Craig Smith, Bedworth; David Robert Edward Walker, Bromsgrove; Gary Woodward, Kidderminster, all of United Kingdom

[73] Assignee: Albright & Wilson UK Limited, West Midlands, United Kingdom

[21] Appl. No.: 09/025,192

[22] Filed: Feb. 18, 1998

[30] Foreign Application Priority Data

Feb. 26, 1997 [GB] United Kingdom ............... 9703951

[51] Int. Cl.[7] ............... C02F 5/14; C02F 11/167; C09K 7/04; C08F 30/02; C11D 7/16
[52] U.S. Cl. ............... 252/389.2; 252/175; 252/389.23; 252/389.62; 106/14.12; 510/534; 507/274; 526/274; 526/278
[58] Field of Search ............... 252/387, 175, 252/389.2, 389.23, 389.62; 549/262; 106/14.05, 14.12, 14.13, 14.14; 510/534; 507/200, 274, 277; 526/274, 278

[56] References Cited

U.S. PATENT DOCUMENTS

| | | | |
|---|---|---|---|
| 5,077,361 | 12/1991 | Hughes et al. | 526/233 |
| 5,376,731 | 12/1994 | Kerr et al. | 525/340 |
| 5,386,038 | 1/1995 | Davis et al. | 549/262 |
| 5,606,105 | 2/1997 | Davis et al. | 562/8 |

FOREIGN PATENT DOCUMENTS

| | | |
|---|---|---|
| 0 479 465 | 4/1992 | European Pat. Off. . |
| 0 491 391 | 6/1992 | European Pat. Off. . |
| 643081 | 3/1995 | European Pat. Off. . |
| 780406 | 6/1997 | European Pat. Off. . |
| 807635 | 11/1997 | European Pat. Off. . |
| 407915 | 12/1973 | U.S.S.R. . |
| 1 458 235 | 12/1976 | United Kingdom . |
| 9611291 | 4/1996 | WIPO . |

OTHER PUBLICATIONS

CAPLUS 1974: 96157.
WPIDS 74–85581V, 1974.
Ludwig Maier, "Organic Phosphorus Compounds 47," Synthesis and Properties of Bis (phosphonylethyl) phosphinates and the Corresponding Acid, *Phosphorus*, 1971, vol. 1, pp. 105–109.
Ludwig Maier, "New organophosphorus complexing agents for calcium and magnesium ions," 1st International Congress on Phosphorus Compounds, Rabat. 1977, pp. 195–199.

*Primary Examiner*—Shean C. Wu
*Attorney, Agent, or Firm*—Frishauf, Holtz, Goodman, Langer & Chick, P.C.

[57] ABSTRACT

The reaction of compounds of the formula:

$$X_2O_3P\ CHY\ CZ_2$$

where Y and each Z are each H, $PO_3X_2$, $SO_3X$ or $CO_2X$ (e.g. vinyl phosphonic acid or vinylidene diphosphonic acid) with hypophosphorous acid in the presence of free radicals provides novel compounds $X_2O_3PCHYCZ_2PO_2XH$ which react with monomers such as vinyl sulphonate, vinyl phosphonate, vinylidene diphosphonate and acrylic acid to form telomers useful for scale inhibition, especially barium scale in oil wells. The polymers show better absorption to rock than PVSA and better thermal stability than random copolymers containing equivalent phosphorus.

31 Claims, No Drawings

PHOSPHINO DERIVATIVES

The present invention relates to novel derivatives of hypophosphorous acid which are of value as, or in the preparation of, polymeric compounds with powerful scale and corrosion inhibiting properties and which are of particular value in the treatment of water used in oil field operations, or in anticorrosive pigments.

Scale and corrosion inhibitors are used to treat a variety of aqueous systems such as boiler water, industrial process water, cooling water and water in central heating and air conditioning systems, to prevent deposition of calcium carbonate, or other alkaline earth metal, scale from hard water systems, or corrosion of metal surfaces by soft water systems. Typically scale and corrosion inhibitors are effective at low concentrations in the range 1 ppm to 500 ppm.

Examples of scaling and corrosion inhibitors include phosphonosuccinic acid, phosphonated polymaleates described in EP 0.491.391,2-phosphono-1,2,4-tricarboxy butane and its salts, 2-hydroxy-2-phosphonoacetic acid and its salts, acetodiphosphonic acid and its salts and amino tris (methylene phosphonic acid and its salts. GB 1.458.235 describes the preparation of water treatment agents from the reaction of acrylic acid with hypophosphorous acid.

A particular problem is sometimes encountered in oil field when sea water is injected into oil bearing strata in order to force the oil to the surface when the gas pressure in the formation is insufficient, e.g. during the latter stages of recovery. If the formation water contains dissovled barium the intereaction with sulphate in the sea water can give rise to severe problems when barium sulphate precipitates as a scale. The problem may be so severe as to block the well and necessitate redrilling. The more commonly used scale inhibitors are often not sufficiently effective to prevent sulphate scaling in such systems especially barium sulphate scaling.

One product which has been found relatively effective is polyvinylsulphonica acid (PVSA). PVSA and its water soluble salts have been injected into the rock formations to inhibit scaling, but are relatively quickly flushed out again. This necessitates continuous renewal of the scale inhibitor, and the use of relatively large amounts of polymer.

EP 0643081 describes an improved scale inhibitor which comprises a copolymer of vinyl sulphonic and vinyl phosphonic acids. The copolymer is weakly adsorbed onto the surface of the minerals in the formation and then gradually released at a rate sufficient to maintain effective scale inhibiting concentrations of copolymer.

In this way the well may be kept scale-free over an extended period after a single injection of copolymer. One disadvantage of the copolymer, however, it is tendency to decompose at the high temperatures which are often encountered in oil wells.

We have now discovered that telomers comprising phosphonate and/or phosphinate groups as part of an end capping group are more thermally stable than copolymers containing equivalent amounts of phosphorus present entirely in comonomers, and are especially effective scale inhibitors with good absorption properties.

In particular we have discovered than vinyl phosphonic acids produce adducts with hypophosphorous acid which can be used as intermediates in the preparation of a range of telomers which are of value as scale and corrosion inhibitors.

The invention provides novel compounds having the formula:

$$X_2O_3P.CHY\ CZ_2\ PO_2XR \quad (I)$$

where X is H or an alkali metal, alkaline earth or other polyvalent metal, ammonium or an organic base, and R is hydrogen, an alkyl moiety or a group, or polymeric chain comprising between 1 and 100,000 groups, said group or groups being derived from at least one unsaturated compounds in which the multiple bond is activated chemically by an adjacent electron withdrawing group, and Y and Z are each hydrogen, a $PO_3X_2$, $SO_3X$ or $CO_3X$ group or an alkyl or aryl moiety.

In particular certain of the novel telomers are of value in preventing barium scale deposition during oil recovery. For instance in the presence of calcium the novel vinyl sulphonate telomers show improved adsorption onto mineral surfaces compared with PVSA and superior thermal stability compared with VPA/VSA copolymer, as well as excellent barium scale inhibition.

The compounds of our invention may exist either as free acids or as their salts. They are normally prepared and used in the form of water soluble salts (e.g. alkali metal salts, especially sodium or potassium salts, or ammonium salts). References herein to the products or their precursors as acids should be construed as including references to the soluble salts where the context permits.

Water insoluble salts of our novel polymers with multivalent metals such as calcium, barium, magnesium, aluminium or iron are useful as pigments for anti-corrosive coatings.

The compounds of the aforesaid formula I where R=H are primarily of value as intermediates for the preparation of polymeric products of the invention.

The preferred intermediates are those of the aforesaid formula I wherein R=H, Y=H, Z=H and X=H, alkali metal or ammonia (1-phosphono-2-phosphinoethane and its salts, herein referred to as PPE) and R=H, Y=$X_2O_3P$, Z=H and X=H, alkali metal or ammonium (1,1-diphosphono-2-phosphinoethane and its salts, herein referred to as DPPE). Other intermediates of value include: R and Z=H, Y=methyl; R and Z=H, Y=phenyl; R and Z=H, Y=$SO_3X$ and R=H, Y=H and one Z=H and the other Z=$SO_3X$ or $PO_3X_2$.

The intermediates, R=H maybe prepared by reacting a vinyl phosphonic acid or salt thereof

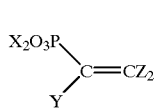

(II)

with hypophosphorous acid or a salt thereof in aqueous solution in the presence of a free radical source.

The free radical source may be a peroxy salt such as an alkali metal (e.g. sodium) persulphate or peracetate, hydrogen peroxide, a hydroperoxide, chlorine dioxide, sodium chlorate, sodium hypochlorite, organotin hydrides, azo compounds such as 4,4'-azobiscyanovaleric acid, electrolysis, ultra violet or other ionising radiation or ultrasound, or any combination of the foregoing.

The amount and rate of formation of free radical generated determines the extent to which the reaction may proceed and the time required.

Preferably the amount of free radical initiator is sufficient to take the reaction to completion in reasonable time (e.g. within 0.25 to 24 hours). Smaller amounts may be used if incomplete reactions can be tolerated. Generally the quantity of free radical required is substantially greater than in normal free radical catalysed reactions. Excess free radical source is, however, preferably avoided on economic grounds and to minimise contamination of the product. Generally the more water present, the more free radical is required in order to complete the reaction. Also, more elevated temperatures may permit the reaction to proceed with less addition of free radicals. We therefore prefer to use a concentrated reaction mixture, e.g. at least 50% and preferably more than 60% total solids. Under these conditions the amount of initiator required is typically from 0.5 to 10 mole %, e.g. 2 to 8 and preferably from 2 to 6 mole % based on the unsaturated reagent. However, if the reaction is performed in a more dilute system, and/or at lower temperatures, higher amount s of initiators such as sodium potassium or ammonium persulphate may be required, typically from 10 to 30% by weight of the unsaturated reagent, e.g. 20 to 25%.

The aqueous solution is preferably from 30 to 65%, e.g. 40 to 60% total solids based on the total weight of the solution. The proportions of the reagents are preferably substantially equimolar lower proportions of vinyl reagent are possible but result in some unreacted hypophosphorous acid. Higher proportions are also possible, but result in some compound in which R=

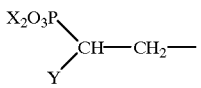

(III)

which is not useful as an intermediate but has other utility, e.g. as a scaling inhibitor.

The temperature required will depend on the catalyst and the concentration of the regents and will be sufficient to initiate and maintain the reaction and to maintain the reaction mixture as a homogeneous, mobile solution. The reaction normally requires temperatures of between 70 and 110° C. However, if an accelerator for the catalyst is used it may be possible to use lower temperatures. The preparation may be effected at alkaline, neutral or acid pH. The pH is typically between 3 and 11 more usually 4 to 10 especially 7 to 9, e.g. 8 to 9. However, higher or lower pHs can be envisaged.

The telomers of our invention are typically prepared by reacting the intermediate of our invention such as PPE or DPPE with a molar excess of one or more monomers with a free radical source in aqueous solution. The monomers are preferably ethylenically unsaturated compounds in which the ethylenic bond is chemically activated by at least one adjacent group such as a sulphonate, phosphonate or carboxylate group. The monomer may alternatively be an activated acetylenic compound. Examples include vinyl sulphonic acid, vinyl phosphonic acid, vinylidene diphosphonic acid, acrylic acid, methacrylic acid, maleic acid, fumaric acid, itaconic acid, aconitic acid, mesaconic acid, citraconic acid, crotonic acid isocrotonic acid, angelic acid, tiglic acid, vinyl alcohol, vinyl chloride vinyl acetate, styrene, styrene-p-sulphonic acid, 2-acrylamido-2-methyl propane sulphonic acid and their water soluble salts. We particularly prefer products in which the polymeric moieties are homopolymers of vinyl sulphonic acid or acrylic acid and copolymers of vinyl sulphonic acid with acrylic and/or maleic acid and/or vinyl phosphonic and/or vinylidene diphosphonic acid. Preferably such copolymers contain a major proportion of vinyl sulphonic acid groups.

The relative molar proportions of the intermediate and the monomer may range from 1:1 to 1:1000 preferably 1:5 to 1:500 especially 1:10 to 1:100, e.g. 1:15 to 1:50. The reaction conditions may be substantially similar to those used for the preparation of the intermediate. Generally however the preferred concentration of reaction mixture is somewhat higher, e.g. 30 to 80% by weight total solids based on the total weight of the reaction mixture, especially 50 to 70% by weight. At the higher concentrations higher temperatuares, e.g. 100 to 140° more preferably 12 to 140° may be required to maintain a pourable solution. The molecular weight of the product is typically up to 200,000. Usually the number of monomer groups per molecule is from 1 to 500, e.g. to 10 to 100. To prepare the telomers we prefer pH between 2 and 9 especially 2 to 6 e.g. 2.5 to 4.

We do not exclude the presence of water miscible solvents. The solvent should contain sufficient water to dissolve the reagents to a substantial extent. The organic solvent may for example comprise methanol, ethanol, iso-propanol, ethylene glycol, propylene glycol, a water soluble oligomer of ethylene or propylene glycol such as diethylene glycol, a water soluble mono- or di- ether or ethylene glycol monomethyl ether, ethylene glycol dimethyl ether, diethylene glycol monoethyl ether or diethylene glycol mono methyl ether, glycerol, a water soluble glyceryl ether, acetone, and/or dioxan. The requirement to dissolve the reagents in the same aqueous based solvent is the main limitation on choice of unsaturated reagent. In cases of difficulty it may be possible to carry out the reaction in anhydrous dioxan.

The reaction may optionally be carried out in a stream of an inert gas such as nitrogen.

The reaction may be carried out batchwise, semi-continuously or continuously, e.g. in a pipe reactor. The free radical source may all be added initially or, preferably, in a plurality of additions, or continuously or semi-continuously throughout the reaction. To maximise the yield of phosphonated product it is sometimes necessary to add the unsaturated reagent, continuously or intermittently during the reaction period to an aqueous solution of the phosphinate.

The products are effective in the presence of chlorine, chlorine dioxide, bromine, hypochlorite, hypobromite and other oxidising biocides. They may therefore be used to treat chlorinate water systems or systems sterilised by other oxidising agents. They are useful in cooling water treatment, treatment of industrial process water, boiler water treatment, desalination plant and for treating water used or produced in oil wells including injection water, producted water, and water used for hydrostatic testing of pipelines.

They are also of value as detergent builders or auxiliary builders, e.g. in conjunction with zeolites, or as metal chelating agents, e.g. in metal extractions, They may be used in aqueous based functional fluids such as hydraulic fluids, lubricants, cutting fluids and oil field drilling muds.

In particular, the compounds and mixtures of the invention may be used in squeeze treatment of oil wells. They are especially effective in preventing barium sulphate scale. For example in oil wells the hole is typically flushed out with aqueous surfactant to provide a water wettable surface and then impregnated with a solution of the inhibitor. The calcium salt may be formed in situ either by calcium in the formation, where the latter comprises limestetone, or by prior, or subsequent, treatment of the hole with an aqueous calcium salt, e.g. where the formation comprises sandstone.

Effective concentrations may typically range from 0.1 to 200 ppm, preferably 0.5 to 100 ppm depending on the nature of the aqueous system. For relatively soft water 1 to 50 ppm, e.g. 1.5 to 20 ppm, most preferably 2 to 10 ppm, may give useful corrosion protection. However for oil field scale prevention where barium sulphate is a problem concentration in the range 5 to 50, especially 8 to 25, e.g. 10 to 20 ppm, are preferred.

Products according to the invention may be used in combination with one another, and/or in conjunction with the other water treatment agents including: surfactants, such as anionic surfactants (e.g. $C_{10-20}$ alkyl benzene sulphonates, $C_{10-20}$ olefin sulphonates, $C_{10-20}$ alkyl sulphates, $C_{10-20}$ alkyl 1 to 25 mole ether sulphates, $C_{10-20}$ parafinsulphonates, $C_{10-20}$ soaps, $C_{10-20}$ alkyl phenol sulphates, sulphosuccinates, sulphosuccinamates, lignin sulphonates, fatty ester sulphonates, $C_{10-20}$ alkyl phenyl ether sulphates, $C_{10-20}$ alkyl ethanolamide sulphates, $C_{10-20}$ alpha sulphofatty acid salts, $C_{10-20}$ acyl sarcosinates, isethionates, $C_{10-20}$ acyl taurides, $C_{10-20}$ alkyl hydrogen phosphates), non-ionic surfactants (e.g. ethoxylated and/or propoxylated $C_{10-20}$ alcohols, ethoxylated and/or propoxylated $C_{10-20}$ carboxylic acids, alkanolamides, amine oxides, and/or $C_{10-20}$ acyl sorbitan and/or glyceryl ethoxylates) amphoteric surfactants (e.g. betaines, sulphobetaines, and/or quaternised imidazolines), and/or cationic surfactants (e.g. benzalkonium salts, $C_{10-20}$ alkyl trimethyl ammonium salts, and/or $C_{10-20}$ alkyl trimethyl or tris(hydroxymethyl) phosphonium slats); sequestrants, chelating agents, corrosion inhibitors and/or other threshold agents (e.g. sodium tripolyphosphate, sodium ethylenediamine tetracetate, sodium nitrilo triacetate, tetra potassium pyrophosphate, acetodiphosphonic acid and its salts, ammonium trismethylene phosphonic acid and its salts, ethylenediamine tetrakis (methylene phosphonic) acid and its salts, diethylenetriamine pentakis (methylene phosphonic) acid and its salts); tolyltriazole and mixtures of nitrate, benzoate HHP and/or PTCB) biocides (e.g. tetrakis (hydroxymethyl) phosphonium salts, formaldehyde, glutaraldehyde); oxidising biocides and/or bleaches (e.g. chlorine, chlorine dioxide, hydrogen peroxide, sodium perborate); foam controlling agents such as silicone antifoams; oxygen scavengers such as hydrazines and/or hydroxylamines; pH controlling and/or buffering agents such as amines, borates, citrates and/or acetates; chromium salts; zinc salts; and/or other water treatment agents such as polymeric dispersants and coagulants including polymaleic, polyacrylic and polyvinylsulphonic acids and their salts, starches and/or carboxy methyl cellulose, and/or molybdates. The invention provides formulations comprising an effective amount of a product of the invention as aforesaid and any of the aforesaid known water treatment agents. Such formulations may, for example, contain from 5 to 95% by weight of a product of the invention and from 5 to 90% by weight of one or more of any of the aforesaid water treatment agents.

According to a further embodiment our invention provides a corrosion inhibiting pigment which is a solid composition which may be prepared by reacting a concentrated aqueous solution of any of the water soluble phosphino compounds according to the invention with a base or salt of calcium, zinc, barium, aluminium or other polyvalent metal and precipitating a solid salt.

According to a further embodiment our invention provides a corrosion inhibiting coating composition containing a pigment according to the invention.

The corrosion inhibiting pigment may be dissolved or dispersed in an anti-corrosive paint, varnish, enamel, lacquer, or other coating formulation. The formulation may comprise a volatile liquid vehicle, such as water or a volatile organic solvent including petroleum spirit, turpentine, ketones, esters and/or aromatic hydrocarbon solvent, and/or a drying oil, such as linseed oil, soya oil, tung oil or dehydrated castor oil, which may optionally be dissolved in said volatile organic solvent or emulsified in said water.

The formulation typically may also comprise a resin, e.g. a polyester, urea formaldehyde, melamine, acrylic, alkyd, polyurethane, vinyl chloride, vinyl acetate, phenolic or epoxy resin dissolved or dispersed therein and/or a dispersed pigment. We prefer that the pigment should be or should comprise other corrosion inhibiting pigments such as red lead, potassium zinc chromate, metallic zinc or aluminium powder and/or that the formulation should contain one or more of the other corrosion inhibitors referred to above in addition to the corrosion inhibiting pigment of the invention.

The coating compositions may additionally contain any of the conventional paint ingredients, including pigments such as titanium oxide, iron oxide, carbon black, phthalocyanine pigments or aluminium stearate, chorinated rubber, polystyrene, silicone, asphalt, wetting agents, dispersants, emulsifiers, biocides, flocculants, marine antifoulants, antifoams, viscosifiers, fire retardants, fluorescers, aerosol propellants, talc, clay and/or plasticisers.

Alternatively the water soluble corrosion inhibitors of the invention may be used to provide a corrosion inhibiting treatment for metal surfaces such as steel, aluminium and aluminium alloys after any machining and prior to storage, coating, electroplating, polishing or etching. Typically the work is coated with an aqueous solution containing at least an operative amount of said corrosion inhibitor, e.g. 10 to 500 ppm preferably 25 to 300, e.g. 20 to 200 especially 25 to 100, more especially 30 to 80.

After contacting with the corrosion inhibiting solution the work may be rinsed and/or subjected to one or more coating or finishing operations such as resin coating, lacquering, enamelling, painting, electrophoretic coating, spattering, vapour deposition, electrodeposition, etching, chemical or electrical polishing or may be put aside for storage.

The work may be greased for storage, but an advantage of the treatment is that greasing and hence subsequent degreasing may be avoided.

The product may be incorporated into solid or liquid detergent compositions. It functions as a stain remover and also may help to stabilise any bleach present and exhibits valuable detergent building action by sequestering calcium. Typically it is added to detergent compositions in amounts of from 0.5 to 20% by weight of the composition.

The liquid detergent of our invention preferably contains 5 to 50%, e.g. 10 to 40% by weight surfactant, 5 to 60%, e.g. 10 to 40% builder, 20 to 75%, e.g. 40 to 70% by weight water and 0.1 to 2.5% of said polymer. The liquid detergent preferably also contains conventional amounts of minor adjuncts including enzymes, soil suspenders such as sodium carboxymethyl cellulose, optical brighteners, dyes, perfumes, preservatives and foam modifiers.

The builders preferably comprises non-phosphate builders such as zeolite, carbonate, citrate, nitrilotriacetate and ethylene diamine tetracetate.

The detergent formulations of the invention may contain from 1% to 90% by weight of surfactant, more usually 2% to 70%, e.g. 3% to 60% especially 4% to 50%, preferably 5% to 40%, more preferably 6% to 30%, most preferably 7% to 20%.

For example the surfactant may be, or may comprise, one or more anionic surfactants such as an alkyl benzene sulphate, alkyl sulphate, alkyl ether sulphate, paraffin sulphonate, olefin sulphonate, alkyl ether sulphonate, alkylphenyl sulphate, alkylphenyl ether sulphate, alkyl sulphosuccinate, alkyl sulphosuccinamate, alkyl isethionate, alkyl sarcosinate, soap, alkyl ether carboxylate, alkyl ether polycarboxylate, alkyl tauride, alkyl phosphate, alkyl ether phosphate or alkyl or thiol capped polyelectrolytes such as an alkylthiol capped polymaleic acid.

All references to "alkyl" groups in this context refer to $C_{8\ to\ 22}$ straight or branched chain alkyl or alkenyl groups.

"Ether" refers to glyceryl, mono- or poly- ethyleneoxy, mono or poly propyleneoxy, or mixed ethyleneoxy/propyleneoxy, glyceryl/ethyleneoxy, glyceryl/propyleneoxy or glyceryl/ethyleneoxy/propyleneoxy. The cation of the aforesaid anionic surfactants is usually sodium but may also be potassium or mono-, di or tri-alkylolamine. Less commonly the cation may be lithium, ammonium, calcium, magnesium, zinc or a mono-di- or tri-alkyl amine such as isopropylamine or trimethylamine.

The surfactant may also be, or may comprise, one or more non-ionic surfactants such as the polyalkoxylated derivatives of alcohol's carboxylic acids, alkyl phenols, alkylamines, alkanolamides, or glyceryl or sorbitan ester, wherein each compound has an "alkyl" group as hereinbefore defined, and the polyalkylene oxy group comprises from 1 to 5 ethyleneoxy and/or propyleneoxy groups.

alternatively the non-ionic surfactant may be an alkanolamide, e.g. a mono- or di-alkanolamide, a lactobionamide, an alkylpolyclycoside or an amine oxide, or an alkly or thiol capped polyvinyl alcohol or polyvinylpyrrolidone, or a sugar ester.

The builder may consist of a phosphino product according to this invention. Alternatively, the builder may comprise such a product together with one or more other builders such as zeolite, sodium tripholyphophate, potassium pyrophosphate sodium or potassium carbonate, sodium citrate, sodium nitrilotriacetate, sodium silicate and or sodium ethylene diamine tetracetate. Thus the product of the invention may constitute from 1% to 100% of the total builder, e.g. 5 to 90% especially 10 to 80%. The balance may comprise an inert solid such as sodium sulphate, or a liquid medium such as water or a low molecular weight polyethylene glycol. The detergent may additionally comprise: up to 5% by weight, e.g. 0.01 to 2% by weight, of optical brightener; up to 5% by weight, e.g. 0.01 to 2% by weight of soil suspending agent such as sodium carboxymethyl cellulose; and up to 6%, more usually up to 2%, by weight, each, or perfume, dye, enzyme, bleach, buffers and other conventional ingredients of solid or liquid detergent composition.

The invention will be illustrated by the following examples. All preparations were carried out under an atmosphere of nitrogen.

EXAMPLE 1

Preparation of PPE

Sodium hydroxide (740.8 g of a 50% solution, 9.26M) was added dropwise to a solution of vinyl phosphonic acid (500 g, 4.63M) in water (700 ml). To this was added sodium hypophosphite monohydrate (490 g, 4.63M). Approximately ⅓rd of this solution was heated to reflux and sodium persulphate (5 g in water, 5 ml) added over 10 minutes. An exotherm was observed. Another ⅓rd of the initial mixture was added to the reaction product of the initial third and the persulphate addition repeated. The final ⅓rd was then also combined with another 5 g of persulphate added at reflux. The reaction mix was cooled. $^{31}P$ nmr indicated 76.2% of the hypophosphite had reacted. This reaction mixture was used directly for further reaction with sodium vinyl sulphonate.

EXAMPLE 2

Preparation of DPPE 480 g tetra-sodium vinylidene diphosphonate (37.4% aqueous solution, 0.47 moles) and 358 g hypophosphorus acid (16% aqueous solution, 0.47 moles) were charged to a reaction vessel and heated to 100° C.

22.3 g sodium persulphate (10% aqueous solution 0.0094 moles) were added via a peristaltic pump addition funnel over 1 hour. The reaction mixture was left to reflux for further 2 hours and allowed to cool. The product contained no unreacted vinyl diphosphonate by $^{31}P$ nmr.

EXAMPLE 3

Preparation of PPE Capped PVSA Telomer (n=10)

Sodium vinyl sulphonate (200 g of a 25% aqueous solution) was added to the vinyl phosphonic acid adduct of Example 1 (20 g of a 46.5% aqueous solution) and the mixture heated to reflux. Water (70 g) was distilled off and sodium persulphate (1 g in 2 ml water) added to the reaction dropwise over a period of 15 minutes. At this point an exotherm was observed. The reaction mixture was then cooled to room temperature and a sample removed for $^{31}P$ nmr which indicated 95% of the vinyl phosphonic acid adduct had reacted to form a telomeric species.

EXAMPLE 4

Preparation of DPPE Capped PVSA Telomer (n=10)

5.0 g tetrasodium vinylidene disphosphonate/hypophosphorous acid adduct of Example 2 (55% solution in water) and 393 g sodium vinyl sulphonate (10 mole equivalents, 25% aqueous solution) were charged to a reaction vessel and 25 ml water removed by distillation to give a paste with 65% solids. The mixture was heated at 120° C. to give mobile solution and 0.02 g sodium persulphate in 0.2 ml water was added and heated for 3 hours. $^{31}P$ nmr showed 80% conversion of phosphorus to product.

EXAMPLE 5

Preparation of DPPE Capped Polyacrylate Telomer (n=11)

A solution of DPPE (85.5 g of a 38% aqueous solution) was heated to 90° C. Acrylic acid (65 g) and sodium persulfate solution (3.9 g in 16.5 g of water) were separated but simultaneously added dropwise over 2 hours to the DPPE. After the addition, the reaction was left for a further 4 hours at 90° C. before being cooled to room temperature, when a sample was removed for $^{31}P$ nmr which indicated that 96% of the adduct had reacted to form polymeric species. The polymer was also characterised using aqueous GPC, which gave a Mw value of 2800 gmol$^{-1}$.

EXAMPLE 6

Preparation of DPPE Capped Acrylic Acid-Solution Vinyl Sulphonate Cotelomer (n=50:50)

Sodium vinyl sulphonate (260 g of a 25% aqueous solution) was concentrated by distilling off 97 g of water. To this solution was added DPPE (10.5 g of a 38% aqueous solution). The mixture was heated to 100° C. and sodium persulphate (2.4 g in 20 g of water) and acrylic acid (36 g) were separately but simultaneously added dropwise over 2 hours. Initially an exotherm was observed. The reaction was than left for a further 3 hours at 100° C., before being cooled to room temperature. $^{31}P$ nmr revealed 100% of the adduct had reacted to form polymeric species. Aqueous GPC gave a bimodal distribution with a Mw value of 8000 gmol$^{-1}$.

EXAMPLE 7

Preparation of DPPE Capped Acrylic Acid-Sodium Vinyl Sulphonate Cotelomer (n=6:6)

Sodium vinyl sulphonate (41.6 g of a 25% aqueous solution) was added to DPPE (223.5 g of a 23% aqueous solution) and the combined solution was concentrated by distilling off 270 g of water. The mixture was heated to 100° C. and sodium persulphate (40 g of a 10% aqueous solution) and acrylic acid (60.5 g) were separately but simultaneously added dropwise over 2 hours. Initially an exotherm was observed. The reaction was then left for a further 3 hours at 100° C., before being cooled to room temperature. $^{31}$P nmr revealed 98% of the adduct had reacted to form polymeric species. Aqueous GPC gave a Mw value of 2200 gmol$^{-1}$.

EXAMPLE 8

Scale Inhibition Under Simulated Oilfield Conditions with Barium Sulphate Test Method Synthetic sea water was prepared from:

| | |
|---|---|
| Na$_2$SO$_4$ | 3.59 g/L |
| NaCl | 50 g/L |
| CH$_3$CO$_2$NH$_4$ | 1 g/L |

Synthetic formation water was prepared from:

| | |
|---|---|
| BaCl$_2$.2H$_2$O | 2.245 g/L |
| NaCl | 50 g/L |
| CH$_3$CO$_2$NH$_4$ | 1 g/L |

The solutions were mixed and passed through a capillary tube.

Inhibitor was dosed into the sulphate solution at a concentration double the desired level so that when the barium and sulphate waters were (50:50 ratio) just prior to entering the capillary tube the desired inhibitor level was achieved in the mix.

The flow was maintained until a rise of pressure indicated tube blocking. Progressively higher concentrations of inhibitor were added until the test ran without blocking for 1 hour, at which point the test was discontinued and the inhibitor rated as passing at the concentration.

The product of Example 3 failed at 15 ppm by weight but passed at 20 ppm by weight. The product of Example 4 failed at 10 ppm but passed at 15 ppm.

For comparison a number of commercial descalers were tested and found to fail at concentrations up to 100 ppm. Most failed at all concentrations up to the limit of the compatibility with the system.

EXAMPLE 9

Compatibility with Gylcol Freeze Inhibitor

The composition of Example 3, diluted was mixed with an equal amount of ethylene glycol (50:50 ratio mix) in order to see if they were compatible. They were and subsequent −20° C. stability testing confirmed that the solution did not freeze solid.

EXAMPLE 10

Scale Inhibition Under Sulphate-Free Conditions

Brines were prepared which duplicated the analysed composition of North Sea brine with the sulphate component removed and two formation waters from North Sea oil fields, as follows:

Composition of sulphate free North Sea Brine:

| | Composition g/L |
|---|---|
| NaCl | 24.074 |
| CaCl$_2$.6H$_2$O | 2.34 |
| MgCl$_2$.6H$_2$O | 11.436 |
| KCl | 0.877 |

Composition of Forties Formation Brine:

| | Composition g/L |
|---|---|
| NaCl | 74.166 |
| CaCl$_2$.6H$_2$O | 14.354 |
| MgCl$_2$.6H$_2$O | 4.213 |
| KCl | 0.709 |
| BaCl$_2$.2H$_2$O | 0.448 |
| SrCl$_2$.6H$_2$O | 1.747 |

Composition of ETAP (Heron) Formation Brine:

| | Composition g/L |
|---|---|
| NaCl | 190.65 |
| CaCl$_2$.6H$_2$O | 229.57 |
| MgCl$_2$.6H$_2$O | 16.14 |
| KCl | 21.73 |
| BaCl$_2$.2H$_2$O | 2.42 |
| SrCl$_2$.6H$_2$O | 3.47 |

In order to determine the limit of compatability of the inhibitor with the brines, the latter were filtered through a 0.45 micron filter and mixed with samples of inhibitor solution in proportions to provide concentrations of inhibitor solution in proportions to provide concentration of inhibitor ranging from 0.01 to 10 in various mixtures of sea water and formation water ranging from 100% sea water to 100% formation water. The mixtures were heated to 40° C. and the temperature raised by 10° C. increments to 120° C. The bottles were inspected for evidence of precipitation after each increment. The product of Example 3 showed no evidence of precipitation with any of the brines under the conditions covered.

EXAMPLE 11

Calcium Carbonate Scale Inhibition

A calcium solution and a bicarbonate solution (containing the inhibitor) were pumped (12.5 mls/minute for both the calcium and bicarbonate solutions giving a combined flow of 25 mls/minute) through a capillary tube which was immersed in a waterbath (60° C.).

When the level of the inhibitor was insufficient to prevent scaling, scale formed within the capillary tube, and the resultant back pressure was recorded. If however there was no increase in back pressure, then scale was not forming in the tube and therefore the level of inhibitor was sufficient to prevent scaling.

Calcium Solution 8.81 grams of calcium chloride dihydrate (CaCL2.2H20) and 1.14 grams 3-[(1,1-dimethyl-2-hydroxyethyl)amino]-2-hydroxy-1-propanesulphonic acid (AMPSA) were made up to 5 liters with deionised water. The pH was adjusted to 9 at room temperature using sodium hydroxide and hydrochloric acid.

Bicarbonate Solution 7.55 grams sodium hydrogen carbonate (NaHCO3) and 1.14 grams AMPSA were made up to 5 liters with deionised water. The pH was adjusted to 9 at room temperature using sodium hydroxide and hydrochloric acid. To one liter of this bicarbonate solution a small volume of inhibitor is added to gain the desired concentration after being mixed with the calcium solution. The pH is then corrected back to 9 pH prior to testing.

The DPPE capped polyacrylate (Example 5) required between 0.2 and 0.3 ppm of total solids to prevent scale forming (100% inhibition).

This performance compares favourably with currently used commercial calcium scale inhibitors.

EXAMPLE 12

Adsorption on Rock

Various end capped inhibitors according to the foregoing examples of the invention were compared with polyvinyl sulphonic acid for their capacity to adsorb onto rock. Samples of each inhibitor were diluted with synthetic sea water to create solutions with a concentration of 2500 mg/L inhibitor solids. For each inhibitor three solutions were prepared and adjusted to 2, 4 and 6 pH using sodium hydroxide and hydrochloric acid.

10 mls of each solution was then mixed with 5 grams of crushed Saltire rock. The rock and solution were heated in an oven at 95° C. for 20 hours, after which the solutions were filtered through a 0.22 micron membrane filter. The supernatant liquor was then analysed for concentration of inhibitor an compared to the concentration of inhibitor in the samples prior to adsorption. The results are shown in the following Table 1.

TABLE 1

| EXAMPLE | pH | % ADSORPTION |
|---|---|---|
| 7 | 2 | 0 |
| 7 | 4 | 0 |
| 7 | 6 | 22 |
| 3 | 2 | 2 |
| 3 | 4 | 3.8 |
| 3 | 6 | 17.3 |
| 4 | 2 | 12.2 |
| 4 | 4 | 12.2 |
| 4 | 6 | 14.3 |
| 6 | 2 | 15.7 |
| 6 | 4 | 9.8 |
| 6 | 6 | 17.6 |
| PVSA | 2 | 0 |
| PVSA | 4 | 0 |
| PVSA | 6 | 0 |
| BLANK | unadjusted | 0 |

EXAMPLE 13

Thermal Stability

Solutions of various scale inhibitors were made up to the desired concentration (500 ppm inhibitor solids) in synthetic sea water. 30 mls of each solution was poured into the teflon liner (internal volume of 50 mls) of a stainless steel bomb. The liquid was then degassed under vacuum for approximately 1 hour followed by a nitrogen sparge for 1 hour. The teflon liners were then sealed and placed into the stainless steel bombs which were placed in an oven at either 150 or 200° C. for 2 weeks. Following this, the bombs were allowed to cool.

Percentage degradation was determined by analysing the increase in orthophosphate content as proportion of total phosphorus. The results were shown in the following Table 2. Three examples of the invention were compared with five random copolymers and two commercial scale inhibitors.

TABLE 2

| INHIBITOR | % Degradation at 150° C. | % Degradation at 200° C. |
|---|---|---|
| Example 3 | 6.8 | 17.3 |
| Example 4 | 1.7 | 12 |
| Example 7 | 10.2 | 12 |
| VPA:VSA (1.9) random copolymer | 50.2 | 41.8 |
| VDPA:VSA (1.9) random copolymer | 38.5 | 68.6 |
| VPA:VSA (1:20) random copolymer | 27.2 | 67 |
| VDPA:VSA:AA (1:4.5:4.5) random copolymer | 19.7 | 75 |
| VPA:VSA:AA (1:4.5:4.5) random copolymer | 55.8 | 94 |
| Sodium diethylenetriamine pentakis (methylenephosphonate) | 75.3 | 91.4 |
| "BELLASOL 540" (RTM) phosphino polyacrylate telomer | 31.6 | 44.6 |

EXAMPLE 14

Bis (diphosphonethyl) Phosphinate

Sodium persulphate (1.6 g, 6.8 mM) was added in portions to a mixture of vinylidene diphosphonic acid tetra sodium salt hydrate (74 g, 0.135M based on 15 moles of water of hydration), and sodium hypophosphite hydrate (7.2 g, 0.067M) held at ca. 100° C. The reaction mixture was cooled to ambient temperature and then a further 16 g of the hydrated VDPA tetrasodium salt followed by re-heating up to 100° C. A further charge of sodium persulphate was then added portionwise. The reaction mix was analysed by 31P nmr which indicated 90 mole % of the phosphorus was present as the bis (diphosphonethyl) phosphinate, $[(Na_2O_3P)_2CH\ CH_2]_2PO_2Na$.

EXAMPLE 15

Barium Scale Inhibition by Example 14

A barium solution and a sulphate solution (containing the inhibitor) were pumped (12.5 mls/minute for both the barium and sulphate solutions giving a combined flow of 25 mls/minute) through a capillary tube which was immersed in a waterbath (90° C.).

Barium Solution 2.245 grams of barium chloride dihydrate, 250 grams sodium chloride and 5 grams ammonium acetate were made up to 5 liters with deionised water. The pH was adjusted to 6 at room temperature using sodium hydroxide and hydrochloric acid.

Sulphate Solution 17.95 grams sodium sulphate, 250 grams sodium chloride and 5 grams ammonium acetate were made up to 5 liters with deionised water. The pH was adjusted to 6 at room temperature using sodium hydroxide and hydrochloride acid. To one liter of this sulphate solution a small volume of inhibitor is added to gain the desired concentration after being mixed with the barium solution. The pH is then corrected back to 6 pH prior to testing.

The bis (diphosphonoethyl) phosphinate of Example 14 required between 10 and 20 ppm of total solids to prevent scale forming (100% inhibition. Commercial products generally require higher concentrations to provide 100% inhibition.

What is claimed is:

1. A composition having the formula:

$$X_2O_3P.CHYCZ_2PO_2XR \qquad (I)$$

where X is selected from the group consisting of H, alkali metal, alkaline earth or other polyvalent metal, ammonium and organic bases capable of forming a water-soluble salt of said compound, and R is selected from the group consisting of hydrogen, a diphosphonoethyl group and a homo- or co-polymeric chain comprising between 1 and 100,000 groups, said groups being derived from at least one unsaturated compound in which the multiple bond is activated chemically by an adjacent electron withdrawing group, and Y and each Z are individually selected from the group consisting of hydrogen, a $PO_3X_2$, $SO_3X$, $CO_2X$, an alkyl moiety and an aryl moiety.

2. A composition according to claim 1, wherein X is selected from the group consisting of H, alkali metal and ammonia, Y is H, each Z is H, and R is H.

3. A composition according to claim 1, wherein X is selected from the group consisting of H, alkali metal and ammonia, Y is $X_2O_3P$—, each Z is H and R is H.

4. A composition according to claim 1, wherein X is selected from the group consisting of H, an alkali metal and ammonia, Y is H or $X_2O_3O$—, each Z is H and R is —$CH_2CYPO_3X_2$.

5. A composition according to claim 1, which is a telomer wherein R is a homopolymeric or copolymeric chain and said unsaturated compound in which the multiple bond is activated chemically by an adjacent electron-withdrawing group consists of at least one monomer selected from the group consisting of unsaturated sulphonic acids, phosphonic acids, carboxylic acids, vinyl alcohol, vinyl chloride, vinyl acetate and their water soluble salts.

6. A composition according to claim 5, which is a telomer wherein said monomer comprises at least one member of the group consisting of vinyl sulphonic acid and its water soluble salts.

7. A composition according to claim 5 wherein said monomer comprises at least one of vinyl phosphonic acid and its water soluble salts.

8. A composition according to claim 5 wherein said monomer comprises at least one of vinylidene diphosphonic acid and its water soluble salts.

9. A composition according to claim 5 wherein said monomer comprises acrylic acid.

10. A composition according to claim 9, wherein said monomer additionally comprises at least one monomer selected from the group consisting of vinyl phosphonic acid, vinylidene diphosphonic acid and their salts.

11. A composition according to claim 5, wherein the monomer comprises at least one member selected from the group consisting of methacrylic acid, maleic acid, fumaric acid, itaconic acid, mesaconic acid, citraconic acid, crotonic acid, isocrotonic acid, angelic acid, tiglic acid, vinyl alcohol, vinyl chloride, vinyl acetate, styrene sulphonic acid, 2-acrylamido-2- methylpropane sulphonic acid and their water soluble salts and from 0 to 4 members selected from the group consisting of vinyl sulphonic acid, vinyl phosphonic acid, vinylidene diphosphonic acid, acrylic acid and their salts.

12. A composition according to claim 4 or claim 5 which is a water insoluble polyvalent metal salt.

13. A composition according to claim 12, wherein said polyvalent metal is selected from the group consisting of calcium, barium, strontium, zinc, magnesium, aluminum, nickel, copper, cobalt and iron.

14. A method of manufacture of a composition according to claim 2 which comprises reacting vinyl phosphonic acid or a salt thereof with hypophosphorous acid or a salt thereof in aqueous solution in the presence of a source of free radicals.

15. A method of manufacture of a telomer which comprises reacting a water soluble compound according to claim 2 with more than 1 molar proportion of an unsaturated compound having an ethylenic or acetylenic bond activated by an adjacent sulphonate, phosphonate or carboxylate group, in aqueous solution in the presence of a free radical source.

16. A method of inhibiting scale formation in an aqueous system which is prone to scale formation, which comprises adding to the system a scale inhibiting amount of a composition according to claim 4 or claim 5.

17. A method of inhibiting scale formation according to claim 16 wherein said system comprises an oil well and means for injecting water into the oil bearing strata.

18. A method according to claim 17, wherein said scale comprises at least one of barium sulphate and barium carbonate.

19. A method of inhibiting corrosion of metal surfaces by aqueous systems having a tendency to cause such corrosion, which comprises adding a corrosion inhabiting amount of a composition according to either claim 4 or 5 to said aqueous systems.

20. A method according to claim 16, wherein said composition is used in a concentration of from 0.1 to 200 ppm.

21. A method according to claim 20 wherein said concentration is form 1.5 to 20 ppm.

22. A corrosion inhibiting coating composition comprising as a pigment, a salt according to claim 12.

23. A coating composition according to claim 22 comprising a volatile liquid vehicle and/or a drying oil.

24. A method of forming a corrosion inhibitory coating on metal surfaces which comprises contacting said surfaces with an aqueous solution of a composition according to claim 1, which is a water soluble salt.

25. A method according to claim 24 wherein said water soluble salt is used in a concentration of from 10 to 500 ppm.

26. A detergent composition comprising a surfactant, a builder and a stain removing amount of a composition according to claim 5.

27. A detergent composition according to claim 26, wherein said water soluble salt is present in an amount of form 0.5 to 20% by weight of the detergent composition.

28. A detergent composition according to claim 26 or claim 27 containing 5 to 60% builder and 20 to 75% water.

29. A water treatment composition comprising from 5 to 95% by weight thereof a composition according to claim 2, and from 5 to 90% by weight of the water treatment composition of at least one other water treatment agent selected from the group consisting of surfactants, sequestrants, chelating agents, corrosion inhibitors, scale inhibitors, biocides, bleaches, foam controlling agents, oxygen scavengers, pH controlling agents, buffers, dispersants and coagulants.

30. A method of manufacture of a composition according to claim 3 which comprises reacting vinylidene diphosphonic acid or a salt thereof with hypophosphorous acid or a salt thereof in aqueous solution in the presence of a source of free radicals.

31. A method of manufacture of a telomer which comprises reacting a water soluble compound according to claim 3 with more than 1 molar proportion of an unsaturated compound having an ethylenic or acetylenic bond activated by an adjacent sulphonate, phosphonate or carboxylate group, in aqueous solution in the presence of a free radical source.

* * * * *